United States Patent [19]
Denardo

[11] Patent Number: 6,165,194
[45] Date of Patent: *Dec. 26, 2000

[54] INTRAVASCULAR FLOW MODIFIER AND REINFORCEMENT DEVICE

[75] Inventor: Andrew J. Denardo, Carmel, Ind.

[73] Assignee: Micrus Corporation, Mountain View, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/122,243

[22] Filed: Jul. 24, 1998

[51] Int. Cl.$^7$ .................................................... A61M 29/00
[52] U.S. Cl. ............................................ 606/191; 623/1
[58] Field of Search ..................... 606/191, 192, 606/194, 195, 198; 623/1, 11, 12

[56] References Cited

U.S. PATENT DOCUMENTS

| | | |
|---|---|---|
| D. 359,802 | 6/1995 | Fontaine . |
| 1,341,052 | 5/1920 | Gale . |
| 1,667,730 | 5/1928 | Green . |
| 2,078,182 | 4/1937 | MacFarland . |
| 2,549,335 | 4/1951 | Rahthus . |
| 3,334,629 | 8/1967 | Cohn . |
| 3,649,224 | 3/1972 | Anderson et al. . |
| 3,868,956 | 3/1975 | Alfidi et al. . |
| 4,494,531 | 1/1985 | Gianturco . |
| 4,512,338 | 4/1985 | Balko et al. . |
| 4,553,545 | 11/1985 | Maass et al. . |
| 4,611,594 | 9/1986 | Grayhack et al. . |
| 4,638,803 | 1/1987 | Rand . |
| 4,655,771 | 4/1987 | Wallsten . |
| 4,670,286 | 6/1987 | Nyilas et al. . |
| 4,718,907 | 1/1988 | Karwoski et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |

(List continued on next page.)

FOREIGN PATENT DOCUMENTS

| | | |
|---|---|---|
| 0 183372 A1 | 6/1986 | European Pat. Off. . |
| 0 282 175 | 9/1988 | European Pat. Off. . |
| 0 382014 A1 | 8/1990 | European Pat. Off. . |
| 0 518 704 A1 | 12/1992 | European Pat. Off. . |
| 0 627 201 A1 | 12/1994 | European Pat. Off. . |
| 0 820 726 A2 | 1/1998 | European Pat. Off. . |
| 0 853 955 A1 | 7/1998 | European Pat. Off. . |
| 592.182 | 7/1925 | France . |
| 4102550 A1 | 8/1991 | Germany . |
| 2 066 839 | 7/1981 | United Kingdom . |
| WO 92/14408 | 9/1992 | WIPO . |
| WO94/03127 | 2/1994 | WIPO . |
| WO 94/16629 | 8/1994 | WIPO . |
| WO94/20044 | 9/1994 | WIPO . |
| WO 95/18585 | 7/1995 | WIPO . |
| WO95/21592 | 8/1995 | WIPO . |
| WO97/48351 | 12/1997 | WIPO . |

OTHER PUBLICATIONS

Copy of International Search Report Relating to PCT/US97/10882 Dated Nov. 6, 1997.

Christos A. Athanasoulis, M.D. The New England Journal of Medicine, May 15, 1980 "Therapeutic Applications of Angiography" pp. 1117–1125 (1 of 2).

Christos A. Athanasoulis, M.D. The New England Journal of Medicine, May 22, 1980 "Therapeutic Applications of Angiography" pp. 1174–1179 (2 of 2).

(List continued on next page.)

*Primary Examiner*—Michael Buiz
*Assistant Examiner*—Vy Q. Bui
*Attorney, Agent, or Firm*—Fulwider Patton Lee & Utecht, LLP

[57] ABSTRACT

An intravascular flow modifier and vascular reinforcement for treatment of aneurysms is formed of a single loop of wire formed into a series of transverse loops and longitudinal connecting sections to configure an essentially cylindrical reinforcement device that still allows, if desired, access to the neck of an aneurysm for insertion of embolic coils and the like.

53 Claims, 2 Drawing Sheets

U.S. PATENT DOCUMENTS

| | | |
|---|---|---|
| 4,813,925 | 3/1989 | Anderson, Jr. et al. . |
| 4,820,298 | 4/1989 | Leveen et al. . |
| 4,830,003 | 5/1989 | Wolff et al. . |
| 4,850,960 | 7/1989 | Grayzel . |
| 4,856,516 | 8/1989 | Hillstead . |
| 4,950,258 | 8/1990 | Kawai et al. . |
| 4,954,126 | 9/1990 | Wallsten . |
| 4,957,479 | 9/1990 | Roemer . |
| 4,957,501 | 9/1990 | Lahille et al. . |
| 4,990,155 | 2/1991 | WIlkoff . |
| 4,994,069 | 2/1991 | Ritchart et al. . |
| 4,994,071 | 2/1991 | MacGregor . |
| 5,015,253 | 5/1991 | MacGregor . |
| 5,019,090 | 5/1991 | Pinchuk . |
| 5,026,377 | 6/1991 | Burton et al. . |
| 5,035,706 | 7/1991 | Giantureo et al. . |
| 5,037,377 | 8/1991 | Alonso . |
| 5,041,084 | 8/1991 | DeVries et al. . |
| 5,041,126 | 8/1991 | Gianturco . |
| 5,061,275 | 10/1991 | Wallsten et al. . |
| 5,064,435 | 11/1991 | Porter . |
| 5,071,407 | 12/1991 | Termin et al. . |
| 5,104,404 | 4/1992 | Wolff . |
| 5,108,407 | 4/1992 | Geremia et al. . |
| 5,116,365 | 5/1992 | Hillstead . |
| 5,122,136 | 6/1992 | Guglielmi et al. . |
| 5,133,731 | 7/1992 | Butler et al. . |
| 5,133,732 | 7/1992 | Wiktor . |
| 5,135,536 | 8/1992 | Hillstead . |
| 5,139,480 | 8/1992 | Hickle et al. . |
| 5,141,502 | 8/1992 | Macaluso, Jr. . |
| 5,147,370 | 9/1992 | McNamara et al. . |
| 5,151,105 | 9/1992 | Kwan-Gett . |
| 5,160,341 | 11/1992 | Brenneman et al. . |
| 5,163,952 | 11/1992 | Froix . |
| 5,171,262 | 12/1992 | MacGregor . |
| 5,176,625 | 1/1993 | Brisson . |
| 5,176,661 | 1/1993 | Evard et al. . |
| 5,183,085 | 2/1993 | Timmermans . |
| 5,186,992 | 2/1993 | Kite, III . |
| 5,197,977 | 3/1993 | Hoffman, Jr. et al. . |
| 5,197,978 | 3/1993 | Hess . |
| 5,203,772 | 4/1993 | Hammerslag et al. . |
| 5,217,483 | 6/1993 | Tower . |
| 5,217,484 | 6/1993 | Marks . |
| 5,222,969 | 6/1993 | Gillis . |
| 5,226,911 | 7/1993 | Chee et al. . |
| 5,226,913 | 7/1993 | Pinchuk . |
| 5,228,453 | 7/1993 | Sepetka . |
| 5,234,437 | 8/1993 | Sepetka . |
| 5,234,456 | 8/1993 | Silvestrini . |
| 5,250,071 | 10/1993 | Palermo . |
| 5,256,146 | 10/1993 | Ensminger et al. . |
| 5,258,042 | 11/1993 | Mehta . |
| 5,304,194 | 4/1994 | Chee et al. . |
| 5,304,200 | 4/1994 | Spaulding . |
| 5,312,415 | 5/1994 | Palermo . |
| 5,314,472 | 5/1994 | Fontaine . |
| 5,322,501 | 6/1994 | Mahmud-Durrani . |
| 5,334,201 | 8/1994 | Cowan . |
| 5,336,205 | 8/1994 | Zenzen et al. . |
| 5,342,300 | 8/1994 | Stefanadis et al. . |
| 5,342,387 | 8/1994 | Summers . |
| 5,350,397 | 9/1994 | Palermo et al. . |
| 5,354,295 | 10/1994 | Guglielmi et al. . |
| 5,354,309 | 10/1994 | Schnepp-Pesch et al. . |
| 5,382,259 | 1/1995 | Phelps et al. . |
| 5,383,887 | 1/1995 | Nadal . |
| 5,395,390 | 3/1995 | Simon et al. . |
| 5,405,377 | 4/1995 | Cragg . |
| 5,413,597 | 5/1995 | Krajicek . |
| 5,415,664 | 5/1995 | Pinchuk . |
| 5,433,723 | 7/1995 | Lindenberg et al. . |
| 5,441,516 | 8/1995 | Wang et al. . |
| 5,443,478 | 8/1995 | Purdy . |
| 5,443,498 | 8/1995 | Fontaine . |
| 5,456,713 | 10/1995 | Chuter . |
| 5,476,505 | 12/1995 | Limon . |
| 5,484,449 | 1/1996 | Amundson et al. . |
| 5,500,013 | 3/1996 | Buscemi et al. . |
| 5,514,176 | 5/1996 | Bosley, Jr. . |
| 5,522,822 | 6/1996 | Phelps et al. . |
| 5,522,836 | 6/1996 | Palermo . |
| 5,527,336 | 6/1996 | Rosenbluth et al. . |
| 5,540,701 | 7/1996 | Sharkey et al. . |
| 5,540,713 | 7/1996 | Schnep-Pesch et al. . |
| 5,549,624 | 8/1996 | Mirigian et al. . |
| 5,549,662 | 8/1996 | Fordenbacher . |
| 5,549,663 | 8/1996 | Cottone, Jr. . |
| 5,554,181 | 9/1996 | Das . |
| 5,562,641 | 10/1996 | Flomenblit et al. . |
| 5,569,245 | 10/1996 | Guglielmi et al. . |
| 5,582,619 | 12/1996 | Ken . |
| 5,601,593 | 2/1997 | Freitag . |
| 5,607,445 | 3/1997 | Summers . |
| 5,609,627 | 3/1997 | Goicoechea et al. . |
| 5,613,981 | 3/1997 | Boyle et al. . |
| 5,618,301 | 4/1997 | Hauenstein et al. . |
| 5,624,461 | 4/1997 | Mariant . |
| 5,632,772 | 5/1997 | Alcime et al. . |
| 5,637,113 | 6/1997 | Tartaglia et al. . |
| 5,639,277 | 6/1997 | Mariant et al. . |
| 5,643,254 | 7/1997 | Scheldrup et al. . |
| 5,643,339 | 7/1997 | Kavteladze et al. . |
| 5,649,949 | 7/1997 | Wallace et al. . |
| 5,653,726 | 8/1997 | Kieturakis . |
| 5,653,727 | 8/1997 | Wiktor . |
| 5,667,522 | 9/1997 | Flomenblit et al. . |
| 5,674,277 | 10/1997 | Freitag . |
| 5,676,697 | 10/1997 | McDonald . |
| 5,690,643 | 11/1997 | Wijay . |
| 5,690,666 | 11/1997 | Berenstein et al. . |
| 5,690,671 | 11/1997 | McGurk et al. . |
| 5,693,085 | 12/1997 | Buirge et al. . |
| 5,713,907 | 2/1998 | Hogendijk et al. . |
| 5,718,724 | 2/1998 | Goicoechea et al. . |
| 5,725,534 | 3/1998 | Rasmussen . |
| 5,733,329 | 3/1998 | Wallace et al. . |
| 5,749,883 | 5/1998 | Halpern . |
| 5,749,891 | 5/1998 | Ken et al. . |
| 5,749,894 | 5/1998 | Engelson . |
| 5,749,918 | 5/1998 | Hogendijk et al. . |
| 5,766,161 | 7/1998 | Globerman . |
| 5,800,526 | 9/1998 | Anderson et al. . |
| 5,824,053 | 10/1998 | Khosravi et al. ........................ 623/1 |
| 5,824,059 | 10/1998 | Wijay . |
| 5,830,229 | 11/1998 | Konya et al. ........................ 606/198 |
| 5,980,514 | 11/1999 | Kupiecki et al. . |

OTHER PUBLICATIONS

Alex Berenstein, M.D. and Irvin I. Kricheff, M.D. "Catheter and Material Selection for Transarterial Embolization: Technical Considerations" Radiology, Sep. 1979; pp. 631–639.

O.A. Battista, et al. Journal of Applied Polymer Science 1967 "Colloidal Macromolecular Phenomena. Part II. Novel Microcrystals of Polymers" pp. 481–498.

Sadek K. Hilal, M.D. et al. Journal of Neurological Surgery "Therapeutic Percutaneous Embolization for Extra–Axial Vascular Lesions of the Head, Neck and Spine" Sep., 1975; pp. 275–287.

Stephen L. Kaufman, M.D. et al. Investigative Radiology, May–Jun. 1978 "Transcatheter Embolization with Microfibrillar Collagen in Swine"; pp. 200–204.

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975 "Selective Arterial Embolization for Control of Massive Upper Gastrointestinal Bleeding" pp. 119–126.

Glenn H. Roberson, et al., American Journal of Radiology, Oct. 1979 "Therapeutic Embolization of Juvenile Angiofibroma" pp. 657–663.

Sidney Wallace, M.D. et al., Cancer, Oct. 1979 "Arterial Occlusion of Pelvic Bone Tumors"; pp. 322–325 & 661–663.

"Mechanical Devices for Arterial Occlusion" by C. Gianturco, M.D., et al., Jul. 1975 pp. 428–435.

"Therapeutic Vascular Occlusion Utilization Steel Coil Technique: Clinical Applications" by Sidney Wallace, et al., Am J. Roetgenol (1976); pp. 381–387.

"Transcatheter Intravascular Coil Occlusion of Experimental Arteriovenous Fistulas", by James H. Anderson, et al., Am J. Roentgenol, Nov. 1977, pp. 795–798.

"'Mini' Gianturco Stainless Steel Coils for Transcatheter Vascular Occlusion" by James H. Anderson, et al., from the Department of Diagnostic Radiology at the University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

INTRAVASCULAR FLOW MODIFIER AND REINFORCEMENT DEVICE

BACKGROUND OF THE INVENTION

1. Field of the Invention

The present invention relates to an intravascular flow modifier and reinforcement device for use within a body vessel, and more particularly, for a device to be used in combination with vasoocclusive devices placed in an aneurysm for the purpose of occluding an aneurysm, whereby the invention provides reinforcement for the area of the blood vessel in the vicinity of the aneurysm.

2. Description of the Related Art

The progress of the medical arts related to treatment of vascular malformations has dramatically improved with the availability of intravascular devices capable of operating entirely within the vasculature. Thus, many highly invasive surgical procedures and inoperable conditions have been treated by the use of an expanding number of devices and procedures designed for those purposes. One particularly useful development in the medical arts has been the ability to treat defects in relatively small arteries and veins, such as those in the neurovascular system, by use of a guiding catheter and the placement of embolic coils and the like in areas where the malformation is likely to cause or has already caused a rupture in the blood vessel. More specifically, it has been found that the treatment of aneurysms by such devices and procedures allows the medical practitioner to avoid otherwise risky medical procedures. For example, when the placement of the defect is in the brain, a great deal of difficulty is presented to treatment of small defects in the blood vessels with conventional surgical techniques. For these reasons, the progress in development of devices to treat such defects has been encouraged and has produced useful results in a wide variety of patients.

One aspect of these surgical treatments is that an aneurysm or other malformation is symptomatic of a general weakening of the vasculature in the area containing the aneurysm, and mere treatment of the aneurysm does not necessarily prevent a subsequent rupture in the surrounding area of the vessel. Moreover, it is often desirable to provide a means to prevent the migration of the vasoocclusive devices, such as coils and the like, out of the aneurysm in the event that the aneurysm has a relatively large neck to dome ratio.

Stents, which are tubular reinforcements inserted into a blood vessel to provide an open path within the blood vessel, have been widely used in intravascular angioplasty treatment of occluded cardiac arteries. In such a case, the stent is inserted after an angioplasty procedure or the like in order to prevent restenosis of the artery. In these applications, the stents are often deployed by use of inflatable balloons, or mechanical devices which force the stent open, thereby reinforcing the artery wall in the clear through-path in the center of the artery after the angioplasty procedure to prevent restenosis. While such procedures may be useful in certain aspects of vascular surgery in which vasoocclusive devices are used, the weakness of the vasculature and the inaccessibility of the interior of the aneurysm from the vessel after the placement of such a stent, places limits on the applicability of such stents in procedures to repair aneurysms, particularly neuro-vascular aneurysms. Furthermore, the use of placement techniques, such as balloons or mechanical expansions of the type often found to be useful in cardiac surgery are relatively less useful in vasoocclusive surgery, particularly when tiny vessels, such as those found in the brain, are to be treated. For these reasons, it would be helpful if a device were available which was compatible with new techniques in vasoocclusive treatment of aneurysms and provides selective reinforcement in the vicinity of the artery, while avoiding any unnecessary trauma or risk of rupture to the blood vessel. The present invention provides these and other advantages.

SUMMARY OF THE INVENTION

Briefly, and in general terms, the invention relates to a three-dimensional wire intravascular flow modifier which is formed of superelastic or shape memory material, which, in its deployed configuration comprises a series of circumferential loops connected by longitudinal portions proceeding in a multiple loop fashion from two free ends of the wire to a closed end loop of the wire. Upon deployment, the device is placed within the vasculature so that it extends from a position proximal to a position distal of the aneurysm to be treated. The device may be arranged so that an open portion of the loop straddles the neck of the aneurysm to allow placement of embolic coils and the like through the opening into the aneurysm. Prior to placement, the device is deformed into a linear form and placed within a guiding catheter, which is used to position the distal end of the device so that the device is pushed out of the guiding catheter by means of a pusher and detached from the pusher by a variety of means to complete placement of the device. After placement of the device, the pusher and catheter are withdrawn.

In a presently preferred method of manufacture of the invention, a single piece of shape memory or superelastic alloys such as nickel titanium alloy, is wound over an essentially cylindrical mandrel into which are formed channels representing the progressive loop configuration of the invention. Alternatively, the mandrel may be cylindrical with pegs inserted in positions representing transitions between the circumferential loops and the longitudinal portions of the wire. A single wire is best wound progressively down the mandrel forming loops and longitudinal transitions until a desired length of the device is reached, at which point the path is retraced similarly to the position at which the device was begun on the mandrel. The wire can then be heat treated on the mandrel to create a shape memory or treated to reach a superelastic state. Thereafter, the device can be taken off of the mandrel and stretched to be inserted into a guiding catheter prior to insertion into the vasculature. The configuration of the present invention provides important advantages over prior art devices in that it eliminates the necessity for balloon or mechanical placement devices which can cause unnecessary trauma to the delicate vasculature which has already been damaged by the presence of the aneurysm. For this reason, the invention is particularly useful to cover and reinforce large neck aneurysms. The presence of the longitudinal portion of the coil dramatically improves the pushability of the device, thereby enhancing the ability to deploy and place the device within the vasculature, an issue of considerable importance if neither balloon nor mechanical placement methods are to be used. Furthermore, the invention can be arranged in a variety of configurations which allow overlapping of the circumferential and longitudinal elements to create particularly desired characteristics to the device and the placement capabilities thereof.

In a second presently preferred embodiment, the device may be configured so that a plurality of wires are used as described above to create more complex configurations and thereby enhance specific aspects of circumferential loop density or longitudinal portion pushability for various applications. Similarly, in another presently preferred embodiment, the density of loops can be varied from proximal to distal end in order to provide a relatively greater circumferential loop density in an area to be placed in a portion of the vasculature which is particularly weak or is threatened by treatment. In yet another presently preferred embodiment, the device may be configured to have a variable diameter to the circumferential elements over the length of the device in order to provide relatively greater circumferential tension against the wall of the vessel in some areas than others.

Another advantage of the present invention is that it may be used in arteries up to renal size while still providing the benefits of placement without the use of balloons or mechanical expansions. One significant benefit in such an application is that the flow through the vessel is never fully occluded by the placement of the device in the invention, and it is possible to place the device from a free flow guiding catheter that is relatively small in diameter compared to the inside diameter of the blood vessel being treated.

While certain features of the invention and its use have been described, it will be appreciated by those skilled in the art that many forms of the invention may be used for specific applications in the medical treatment of deformations of the vasculature. Other features and advantages of the present invention would become apparent from the following detailed description taken in conjunction with the accompanying drawings, which illustrate by way of example, the principles of the invention.

DETAILED DESCRIPTION OF THE PREFERRED EMBODIMENTS

As shown in the exemplary drawings, which are provided for the purposes of illustration and not by way of limitation, the device of the present invention is designed to be deployed intravascularly without the necessity of balloons or other expansive elements and can be deployed from a guiding catheter directly into the area to be treated. The intravascular device of the present invention is particularly useful for treatment of damaged arteries incorporating aneurysms and the like, particularly those which are treatable by the use of embolic coils or other embolic devices or agents used to occlude the aneurysm. More particularly, the device of the invention is particularly well adapted to use with the types of catheters used to place such embolic coils in aneurysms, and the device may be used to reinforce the area in the vicinity of the aneurysm while allowing placement of one or more embolic coils through the gaps in the stent, while assisting in the retention of the embolic devices within the dome of the aneurysm.

Figure 1:
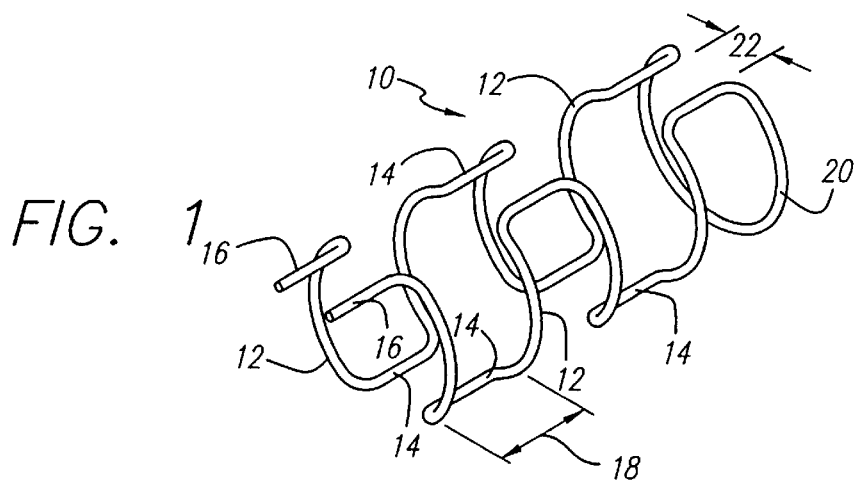
FIG. 1 is a perspective view of a deployed device configured according to the invention.

As illustrated in FIG. 1, one presently preferred embodiment of the present invention 10 can be configured as a series of circumferential loops 12 connected by longitudinal connecting sections 14 to progressively form an essentially cylindrical intravascular device 10 out of a single loop of wire. More specifically, the device is configured of a single piece of wire in which the free ends are placed in close proximity and a first linear section 16 extends axially, and in which the linear wire sections 14 are parallel and longitudinal with the ultimate approximately cylindrical configuration of the device. The wire is then formed into a pair of circumferential sections 12 extending in semi-circular arcs to a position in which a transition into a second pair of parallel elements 14 are formed for a second distance 18 at which they transition back to another pair of circumferential loops 12 and then proceeding sequentially in such a sequence towards an end loop 20 forming the end of the stent. While this configuration is described in the context of a wire, those skilled in the art will realize that other configurations of the material used to form the device, including foils and laminates, are within the scope of the invention. In the presently preferred embodiment, the wire of the device is made of a superelastic material such as a nickel titanium alloy to allow for easy insertion of the device within the guiding catheter. Other materials, such as shape memory alloys, may also be used to provide for the dual purposes of ease of insertion into the guiding catheter and formation upon deployment into the desired shape of the device. One material that is contemplated as a wire from which the device can be made is a stranded cable including one or more radiopaque strands, or which has radiopaque markers deployed along its length. Such a stranded cable can be made of a variety of materials including stainless steel, shape memory alloy, superelastic alloy, platinum or the like or combinations thereof.

The invention provides numerous important advantages in the treatment of vascular malformations, and particularly malformations which include the presence of aneurysms. Since the device does not represent an essentially solid tubular member, and does not require the use of a balloon or other mechanical device for deployment, it is capable of deployment from a guiding catheter which need not occlude the artery as it is put into a position from which to deploy the device. Furthermore, the device upon deployment can reinforce the artery without occluding access to the aneurysm, thus allowing the device to be deployed prior to the placement of embolic coils or the like in the aneurysms. Alternatively, depending on the nature of the vascular defect, the embolic coils or other embolic occlusive or other vasoocclusive devices can be placed and the device deployed thereafter to hold the devices in the aneurysm. By use of the invention, a variety of densities may be provided in the coil to coil distance, thus assisting in the treatment of different vascular malformations.

The present invention contains numerous advantages over the prior art, including enhanced pushability without creating circumferential stress from the loop section, as is often found in the case of coil-type intravascular flow modifiers known in the prior art. More specifically, the conformity of the device to the vascular walls is enhanced by the gaps in the loops 22 where the parallel sections are contained, and characteristics of the device such as loop strength and the resilience of the device are controlled by the radii 24 of the transitions to the longitudinal sections 14 the diameter of the wire and the distance between the parallel sections and the loops from which the device is formed. Thus, the invention provides a wide variety of performance characteristics that can be designed as part of the stent configuration.

Figure 2:
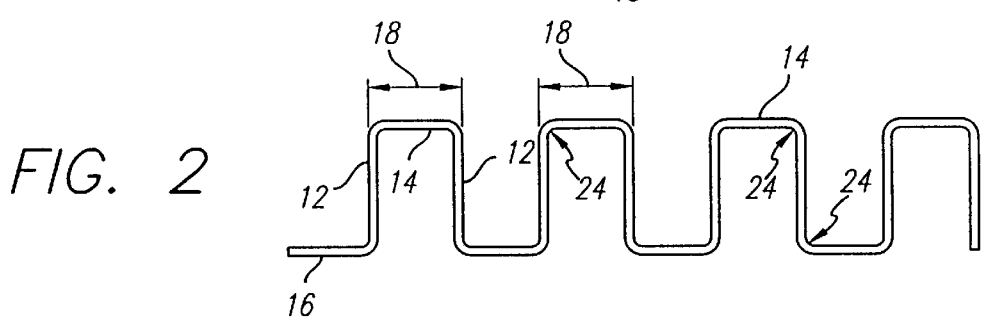
FIG. 2 is a side view of the deployed device of FIG. 1.
Figure 3:
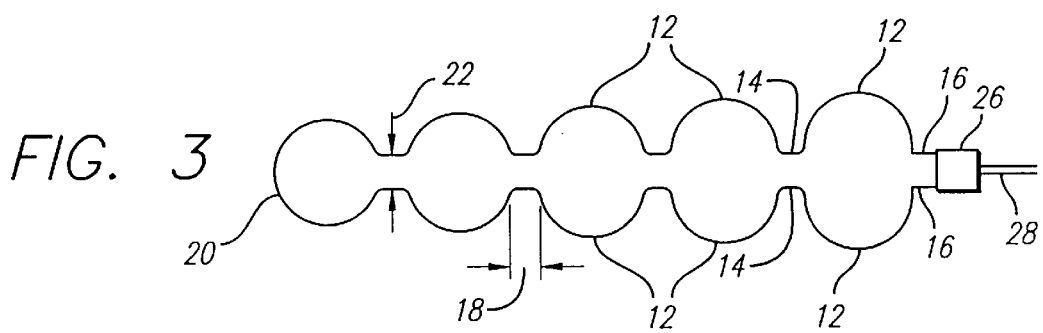
FIG. 3 is a plan view of a partially deployed device of the invention.
Figure 4:
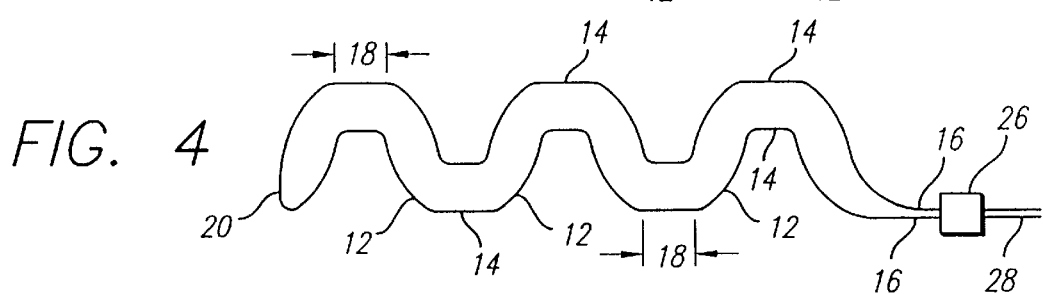
FIG. 4 is a side elevational view of the partially deployed device of FIG. 3.
Figure 5:
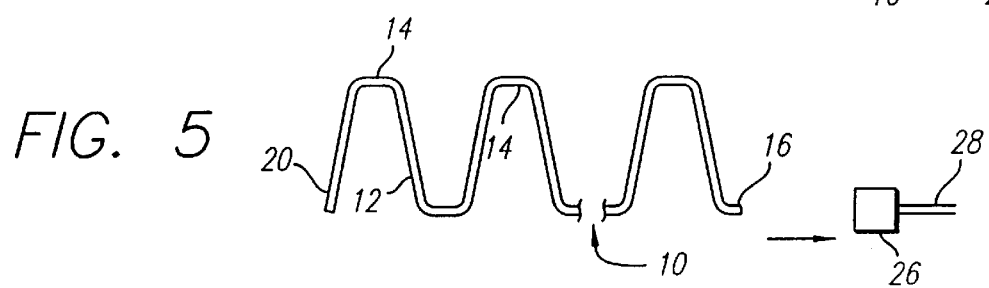
FIG. 5 is a side elevational view of the device showing the deployment connector being released from the device.

As shown in FIG. 2, the deployed device here illustrated in a side view, includes numerous longitudinal elements 14 and circumferential loops 12, the spacing of which can be varied as described above. As illustrated in FIG. 3, the device, prior to full deployment, can be made into an essentially flat configuration in which the free ends of the device are connected to the deployment device 26 on the distal end of a pusher 28 which fits within the guiding catheter (not shown). In this configuration, it can be seen that the circumferential loops 12 are connected by the short linear transitions 14 between the loops which become essentially parallel with the longitudinal axis of the device in the deployed configuration. FIG. 4 is an illustration of a partially deployed device in which the coils 12 have begun to assume their circumferential position within an artery. FIG. 5 illustrates the detachment of the device 10 from the distal end of the pusher showing the device beginning to assume its final deployed position.

Figure 6:
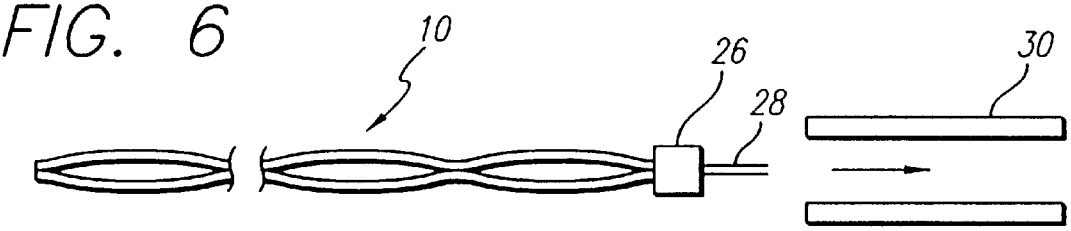
FIG. 6 is a top elevational view of the device configured for installation in a guiding catheter.

FIG. 6 illustrates the initial placement of the device 10 when made of superelastic or shape memory material in which it is first attached to the end of the pusher and the pusher is then pulled into the guiding catheter 30, with the device assuming an essentially linear loop of wire that can then easily fit within the guiding catheter prior to deployment. Upon deployment, the pusher is used to extend the free end of the device from the guiding catheter in an area of the vasculature to be treated.

Figure 7:
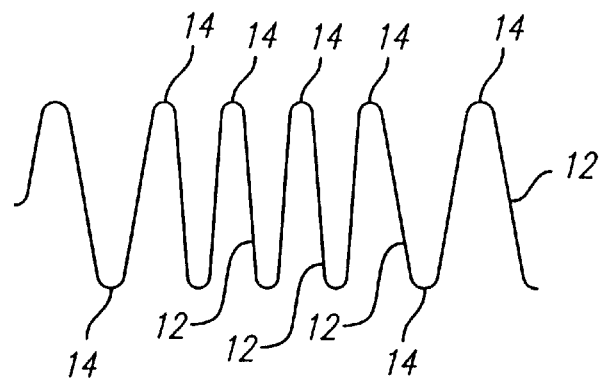
FIG. 7 is a side elevational view of a deployed device illustrating a second preferred embodiment in which the coil of the device are more densely located in the desired portion of the stent.

FIG. 7 illustrates one configuration of the device 10 of the present invention in which the device can be formed to have shorter connecting parallel sections 14 between the loops 12 and thus provide a higher degree of reinforcement in this specific area. Such a configuration has numerous benefits depending on the topology of the damage to the artery, and can provide benefits for certain types of treatment therapies.

Figure 8:
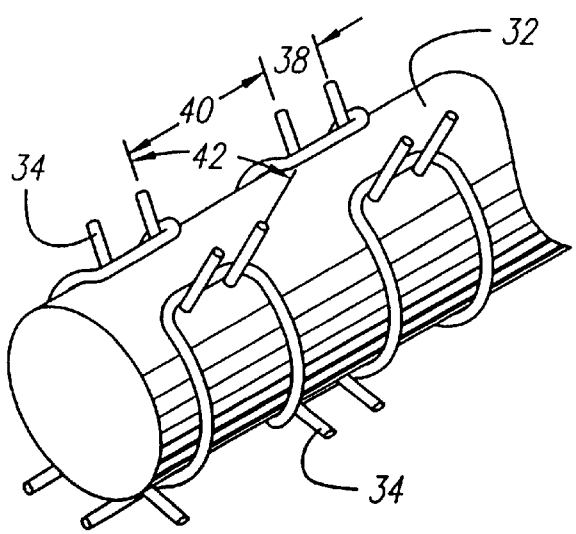
FIG. 8 is an illustration of a mandrel upon which the device is formed in one preferred embodiment of the method of manufacture of the device.

The present invention may be formed in a number of ways, but there are presently two preferred methods of manufacture. In a first preferred method illustrated in FIG. 8, a longitudinal mandrel 32 made of tungsten, ceramic or other heat resistant material has inserted into it pegs 34 of heat resistant material around which the wire to be formed into the device are wound. The diameter of the pegs 36 and the spacing of the pegs 38, 40, 42 may be altered in order to provide certain characteristics that are desired in the stent as it is formed. Alternatively, the mandrel can have a grooved configuration formed into it in which the wire is placed prior to heat treatment.

From the above, it may be seen that the present invention provides significant benefits to the treatment of vascular malformations, and particularly aneurysms in the neurovasculature. Importantly, the invention is particularly advantageous when used in combination with vasoocclusive devices placed in the aneurysm by intravascular procedures.

It will be apparent from the foregoing that while particular forms of the invention have been illustrated and described, various modifications can be made without departing from the spirit and scope of the invention. Accordingly, it is not intended that the invention be limited, except as by the appended claims.

I claim:

1. An intravascular flow modifier and vascular reinforcement device to be used in the intravascular treatment of blood vessels, comprising:
    an elongate section of resilient material having a pre-deployed essentially flat configuration and a deployed configuration of a generally cylindrical device in which the two free ends are attached to deployment means at the distal end of a pusher for deploying said device in the vasculature of a patient, are parallel to one another and extend distally from a proximal end of the device, thereafter transitioning at a first predetermined point to a first essentially circumferential loop for a distance less than half of the circumference of the device, thereafter transitioning to a longitudinal section for a predetermined length to a second predetermined point, thereafter transitioning to a second essentially circumferential loop and proceeding similarly to the distal end of the device.

2. The device of claim 1 wherein said elongate section of resilient material is made of a superelastic material.

3. The device of claim 1 wherein said device is made of a shape memory material.

4. The device of claim 2, wherein the superelastic material is a nickel-titanium alloy.

5. The device of claim 3, wherein said shape memory material is a nickel titanium alloy.

6. The device of claim 3, wherein said shape memory material is a shape memory polymer.

7. The device of claim 1 wherein the longitudinal sections of the elongate section of resilient material from which the device is formed are parallel to one another and to a longitudinal axis of the device and are spaced apart by a predetermined distance.

8. The device of claim 1, wherein said first and second essentially circumferential loops are spaced apart distally along the device by a predetermined distance sufficient to allow passage of an embolic coil between said first and second essentially circumferential loops.

9. The device of claim 1, wherein said longitudinal sections are angled to one another to thereby provide an essentially trapezoidal opening in said device.

10. The device of claim 1 wherein the lengths of said longitudinal sections are varied to vary the number of loops contained within a given length of the device.

11. The device of claim 1 wherein the diameter of said loops is varied to allow said device to modify the blood flow characteristics in the vessel in which the device is placed.

12. The device of claim 1, wherein said loops are of different radii from one another.

13. The device of claim 1, wherein said device is formed of a length of material having a non-circular cross section.

14. The device of claim 1, wherein said circumferential loops are formed into an arcuate curve, the radius of said curve varying over the length of the loop.

15. The device of claim 1, wherein the transitions of the circumferential loops to the longitudinal sections have a predetermined radius.

16. The device of claim 1, wherein the distal end of the device is a loop comprising a continuous loop extending from the most distal longitudinal sections.

17. The device of claim 2, wherein said elongate section of resilient material is a stranded cable.

18. An intravascular flow modifier and vascular reinforcement device to be used in the treatment of vascular malformations, comprising;
    a plurality of semi-circular loops formed from a long slender piece of resilient material, said resilient material having an essentially flat pre-deployed configuration having two free ends attached to deployment means at the distal end of a pusher for deploying said device in the vasculature of a patient and a deployed substantially cylindrical configuration of a series of essentially longitudinal sections between said loops, said longitudinal sections connecting said semi-circular loops, said longitudinal sections including radii at the transitions between said longitudinal sections and said semi-circular loops, said longitudinal sections and said semi-circular loops proceeding distally from a proximal point to the distal end of said device, whereby said semi-circular loops and said longitudinal elements combine in said deployed configuration to form an essentially cylindrical reinforcement for use in a damaged portion of the vasculature.

19. The device of claim 17 wherein said long slender piece of resilient material is made of a superelastic material.

20. The device of claim 17 wherein said device is made of a shape memory material.

21. The device of claim 19, wherein the superelastic material is a nickel-titanium alloy.

22. The device of claim 20, wherein said shape memory material is a nickel titanium alloy.

23. The device of claim 20, wherein said shape memory material is a shape memory polymer.

24. The device of claim 18, wherein said long slender piece of resilient material is a stranded cable.

25. The device of claim 24, wherein said stranded cable comprises at least one strand of superelastic material.

26. The device of claim 18 wherein the longitudinal sections of the long slender piece of resilient material from which the device is formed are parallel to one another and to a longitudinal axis of the device and are spaced apart by a predetermined distance.

27. The device of claim 18, wherein said semi-circular loops are spaced apart distally along the device by a predetermined distance sufficient to allow passage of an embolic coil between said semi-circular loops.

28. The device of claim 18, wherein said longitudinal sections are angled to one another to thereby provide an essentially trapezoidal opening in said device.

29. The device of claim 18 wherein the lengths of said longitudinal sections are varied to vary the number of loops contained within a given length of the device.

30. The device of claim 18 wherein the diameter of said loops is varied to allow said device to modify the blood flow characteristics in the vessel in which the device is placed.

31. The device of claim 18, wherein said loops are of different radii from one another.

32. The device of claim 18, wherein said device is formed of a length of material having a non-circular cross section.

33. The device of claim 18, wherein said semi-circular loops are formed into an arcuate curve, the radius of said curve varying over the length of the loops.

34. The device of claim 18, wherein the transitions of the semi-circular loops to the longitudinal sections have a predetermined radius.

35. The device of claim 18, wherein the distal end of the device is a loop comprising a continuous loop extending from the most distal longitudinal sections.

36. An intravascular flow modifier and vascular reinforcement device to be used in the treatment of aneurysms, comprising:

a plurality of pairs of longitudinal elements connecting semi-circular loops, the loops and longitudinal sections being formed of a single wire, progressing from free ends of a pair of longitudinal elements at a proximal end of the device and extending distally to define an essentially cylindrical reinforcement;

said longitudinal elements spaced apart and said cylindrical elements spaced apart to provide openings through which a vasoocclusive device can be introduced from an area inside said device to an area outside said device and within an aneurysm to be treated, said device being capable of being formed into an essentially linear configuration for insertion into a guiding catheter, an essentially flat pre-deployed configuration, and a substantially cylindrical deployed configuration; and a release means at the proximal end of said device attaching said device to a pusher within the catheter and which may be used to push the device out of the catheter when the catheter has reached a predetermined position within the vasculature, the two free ends being attached to said release means at the distal end of a pusher for deploying said device in the vasculature of a patient.

37. The device of claim 36 wherein said wire is made of a superelastic material.

38. The device of claim 36 wherein said device is made of a shape memory material.

39. The device of claim 37, wherein the superelastic material is a nickel-titanium alloy.

40. The device of claim 38, wherein said shape memory material is a nickel titanium alloy.

41. The device of claim 38, wherein said shape memory material is a shape memory polymer.

42. The device of claim 36 wherein the longitudinal sections of the wire from which the device is formed are parallel to one another and to a longitudinal axis of the device and are spaced apart by a predetermined distance.

43. The device of claim 36, wherein said semi-circular loops are spaced apart distally along the device by a predetermined distance sufficient to allow passage of an embolic coil between said loops.

44. The device of claim 36, wherein said longitudinal sections are angled to one another to thereby provide an essentially trapezoidal opening in said device.

45. The device of claim 36 wherein the lengths of said longitudinal sections are varied to vary the number of loops contained within a given length of the device.

46. The device of claim 36 wherein the diameter of said loops is varied to allow said device to modify the blood flow characteristics in the vessel in which the device is placed.

47. The device of claim 36, wherein said loops are of different radii from one another.

48. The device of claim 36, wherein said device is formed of a length of material having a non-circular cross section.

49. The device of claim 36, wherein said device is formed from a multistranded cable.

50. The device of claim 49, wherein said multistranded cable includes at least one strand made of a nickel-titanium alloy.

51. The device of claim 36, wherein said semi-circular loops are formed into an arcuate curve, the radius of said curve varying over the length of the loop.

52. The device of claim 36, wherein the transitions of the semi-circular loops to the longitudinal sections have a predetermined radius.

53. The device of claim 36, wherein the distal end of the device is a loop comprising a continuous loop extending from the most distal longitudinal sections.

* * * * *

UNITED STATES PATENT AND TRADEMARK OFFICE
CERTIFICATE OF CORRECTION

| | | |
|---|---|---|
| PATENT NO. | : 6,165,194 | Page 1 of 1 |
| APPLICATION NO. | : 09/122243 | |
| DATED | : December 26, 2000 | |
| INVENTOR(S) | : Andrew J. Denardo | |

It is certified that error appears in the above-identified patent and that said Letters Patent is hereby corrected as shown below:

On the title page item (56), line 3, under "OTHER PUBLICATIONS", add the following:
--Copy of International Search Report Regarding PCT/US99/16105, Dated November 11, 1999--.

Signed and Sealed this

Twenty-fifth Day of December, 2007

JON W. DUDAS
*Director of the United States Patent and Trademark Office*